United States Patent [19]

Barton et al.

[11] 4,193,917

[45] Mar. 18, 1980

[54] CHEMICAL COMPOUNDS

[75] Inventors: Derek H. R. Barton, London; Alan G. Long; Brian E. Looker, both of Greenford; Edward M. Wilson, Bowness-on-Windermere; William G. Elphinstone, Stoke Poges, all of England

[73] Assignee: Glaxo Laboratories, Limited, Greenford, England

[21] Appl. No.: 713,649

[22] Filed: Aug. 12, 1976

Related U.S. Application Data

[62] Division of Ser. No. 167,876, Jul. 30, 1971, Pat. No. 3,991,069.

[30] Foreign Application Priority Data

Jul. 31, 1970 [GB] United Kingdom ............... 37186/70
Nov. 3, 1970 [GB] United Kingdom ............... 52289/70

[51] Int. Cl.$^2$ ............................................. C07D 205/06
[52] U.S. Cl. ................................................. 260/239 A

[58] Field of Search ................... 260/239 A, 239.3 A, 260/239 AL

[56] References Cited

U.S. PATENT DOCUMENTS 3,275,626  9/1966  Morin et al. ..................... 260/239 A

FOREIGN PATENT DOCUMENTS 1355330  6/1974  United Kingdom ............... 260/239 A

*Primary Examiner*—Glennon H. Hollrah
*Assistant Examiner*—D. B. Springer
*Attorney, Agent, or Firm*—Bacon & Thomas

[57] ABSTRACT

Novel semisynthetic β-lactam intermediates of use in the production of cephalosporins, penicillins and related β-lactam antibiotic compounds are provided. The novel compounds are prepared from β-lactams obtained by cleavage of the 1,2-sulphur-carbon bond of a penicillin 1-oxide (with subsequent internal or external trapping of the sulphur atom to leave a residual substituent as the β-lactam nitrogen) by removal of the said residual substituent by an oxidative cleavage reaction.

10 Claims, No Drawings

CHEMICAL COMPOUNDS

This application is a division of application Ser. No. 167,876, filed July 30, 1971 and now U.S. Pat. No. 3,991,069.

This invention relates to a process for the production of novel semisynthetic intermediates or relay compounds of use in the production of cephalosporins, penicillins and related β-lactam antibiotic compounds.

The first total synthesis of a cephalosporin antibiotic was achieved by R. B. Woodward (J.A.C.S. 1966, 88, (4), 852) starting from L(+)-cysteine and proceeding via about eight synthetic steps to a β-lactam (i) which was then converted into a cephem (iii) by the following reaction sequence.

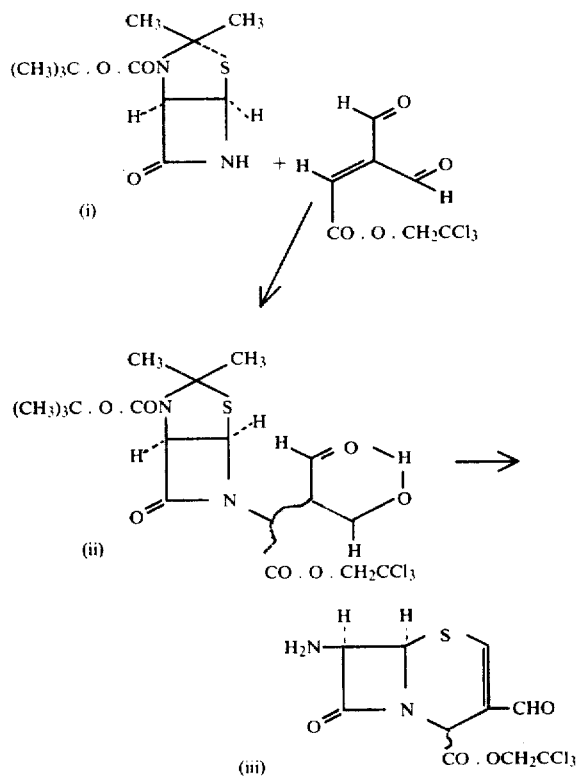

The compound (i) thus constitutes a valuable intermediate in the preparation of cephalosporins and other β-lactam antibiotics; by reaction with an analogous aldehyde reagent it is also possible to convert (i) into a penicillin and it will be appreciated that in this way penicillins having varying substitution in the 5-membered ring can be produced. Similarly by replacing the 2,2,2-trichloroethyl 3,3-diformylacrylate reagent by suitably substituted alternatives, a series of cephalosporin analogues can be prepared.

R. B. Woodward started from L(+)-cysteine in order to achieve a total synthesis. However, this material is relatively expensive and even more significantly, its conversion into a β-lactam of the required sterochimical configuration requires extremely careful control of the stereochemistry at several points.

The present invention is based on the finding that the 1,2-bond of a penicillin 1-oxide can be cleaved with subsequent trapping of the sulphur atom to yield β-lactam compounds which can be converted into a wide range of bicyclic structures such as cephams, cephems and penams. When the penicillin 1-oxide is cleaved with a trivalent phosphorus reagent, the sulphur atom will be internally trapped by the carbonyl group of the 6-acylamido group present to form a thiazoline unless the reaction is effected in the presence of an acylating agent in which case the sulphur atom will be externally trapped to yield an S-acyl compound. Externally trapped compounds can also be prepared by cleaving the penicillin 1-oxide with a thiophilic sulphur nucleophile, and in particular a thiol, whereby the S atom is incorporated in a disulphide bond. Such disulphides can be converted if desired into corresponding thioethers.

All these conversions are described in copending Applications by Underwood and Hewitt; Underwood and Long; Barton, Underwood, Looker, Hewitt and Taylor; Barton, Sammes, Hewitt, Looker and Underwood; and Barton, Underwood, Looker and Hewitt: all filed on July 30, 1971, Ser. Nos. 167,847, now abandoned; 167,874, now Pat. No. 3,900,487; 167,848, now U.S. Pat. No. 3,872,086; 167,875, now abandoned and 167,849, now U.S. Pat. No. 3,927,013, respectively. One advantage of these procedures is that by starting from penicillins it is possible to effect a conversion to compounds closely similar to Woodward's compound (i) more readily and in fewer stages than the production of (i) from L-(+)-cysteine and the β-lactam retains the required steric configuration whereas close and difficult steric control is required in the Woodward syntheses. Furthermore, penicillins, particularly penicillins G and V, are generally cheaper to produce, e.g. by fermentation, than L-(+)-cysteine.

The thiazolines prepared according to the present invention may be subsequently converted, by reduction and N-protection, into thiazolidines closely analogous to Woodward's compound (i) and which differ therefrom merely by the replacement of the gem-dimethyl grouping by hydrogen and a residue derived from the original 6-acylamido group. The reduction may, for example, be effected with aluminium amalgam and water as described in copending application Ser. No. 167,874, now U.S. Pat. No. 3,900,487. Such compounds may be reacted in exactly the same way as Woodward's compound (i) to give Woodward's compounds (ii) and (iii). Woodward's compound (iii) can be converted into an active antibiotic by N-acylation, e.g. with the group PhCH$_2$CO, and reductive cleavage of the 4-ester group.

Compounds in which the sulphur atom of penicillin derivatives has been externally trapped may be reacted at the sulphur and β-lactam nitrogen atoms by the methods now described in copending applications Ser. Nos. 167,848 now U.S. Pat. No. 3,872,086; 167,875 now abandoned and 167,849 now U.S. Pat. No. 3,927,013 to give bicyclic structures, such as cephems and penams, having antibiotic activity.

In both internal and external trapping, the penicillin 1-oxides are cleaved to yield compounds of the formula III

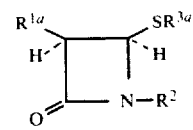

[wherein $R^2$ is a group

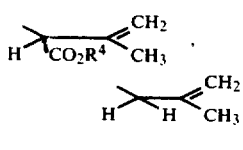
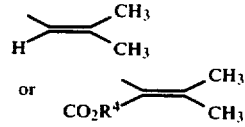

where $R^4$ is hydrogen or a carboxyl blocking group and $R^{1a}$ and $R^{3a}$ represent groups $R^1$ and $R^3$ respectively where $R^1$ is a blocked amino group including a group of formula —NHCOR (where —COR is an acyl group containing 1 to 21 carbon atoms) and $R^3$ is an acyl group, an aliphatic, aromatic or araliphatic group or a group —$SR^5$ (where $R^5$ is an aliphatic, araliphatic, cycloaliphatic or aromatic group containing from 1 to 20 carbon atoms) or a group of formula

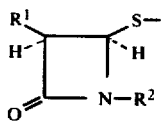

(where $R^1$ and $R^2$ are as defined above) or $R^{1a}$ and $R^{3a}$ together represent the group

where R is the residue of an acyl group —COR which acyl group has from 1 to 21 carbon atoms, the carbon atom of the group

being bonded to the sulphur atom of the compound of formula III].

It will be noted that the compounds of formula III carry a side-chain at the β-lactam nitrogen and in order to functionalise the β-lactam nitrogen atom as in Woodward's compound (ii), this side-chain must be removed. We have found that this can readily be achieved by oxidative cleavage.

According to one feature of the present invention there is provided a process for the preparation of compounds of the general formula

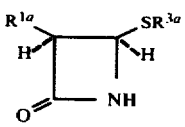

[wherein $R^{1a}$ and $R^{3a}$ represent groups $R^1$ and $R^3$ respectively where $R^1$ is a blocked amino group including a group of formula —NHCOR (where —COR is an acyl group containing 1 to 21 carbon atoms) and $R^3$ is an acyl group, an aliphatic, aromatic or araliphatic group or a group —$SR^5$ (where $R^5$ is an aliphatic, araliphatic, cycloaliphatic or aromatic group containing from 1 to 20 carbon atoms) or a group of formula

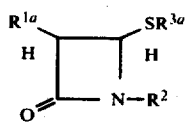

(where $R^1$ is as defined above) or $R^{1a}$ and $R^{3a}$ together represent the group

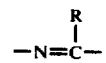

where R is the residue of an acyl group —COR which acyl group has from 1 to 21 carbon atoms, the carbon atom of the group

being bonded to the sulphur atom of the compound of formula I] which comprises subjecting to oxidative cleavage a compound of formula

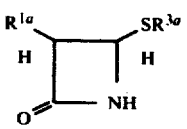

as hereinbefore defined. The definition "acyl" for $R^3$ includes groups such as sulphonyl, sulphinyl and phosphoryl.

According to a further feature of the present invention there are provided compounds of the general formula

wherein $R^{1a}$ is a blocked amino group including a group of formula —NHCOR (where —COR is an acyl group containing 1 to 21 carbon atoms) and $R^{3a}$ is an acyl group or $R^{1a}$ and $R^{3a}$ together represent the group

where R is the residue of an acyl group —COR which acyl group has 1 to 21 carbon atoms, the carbon atom of the group

being bonded to the sulphur atom of the compound of formula I. Compounds of formula I in which $R^3$ is other than an acyl group are described and claimed in copending Applications Ser. Nos. 167,848 and 167,875. An alternative procedure for the preparation of compounds of formula I in which $R^{1a}$ and $R^{3a}$ form a group

is set out in the copending Application by Underwood and Hewitt of even date herewith (Part 2/4).

The oxidative cleavage of the side-chain $R^2$ in compounds of formula III in general proceeds either by allylic oxidation of compounds of formula III in which $R^2$ is the group

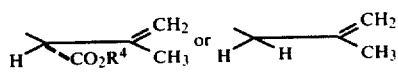

or oxidation of compounds in which $R^2$ is

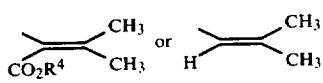

to a derivative carrying an oxygen function at the carbon atom attached to the β-lactam nitrogen. The reagents used will thus be appropriate to such oxidations. In both types of oxidation the introduction of an oxygen function causes instability of the whole side-chain.

For the oxidation of compounds of formula III in which $R^2$ is

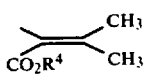

preferred oxidising agents include ozone or a permanganate, e.g. an alkali metal or alkaline earth metal permanganate such as potassium permanganate, permanganates being preferably reacted in the presence of magnesium sulphate as a buffer. These reagents have the advantage of showing no tendency to oxidise the thiazoline sulphur atom and ozone has the merit of producing a gaseous product, oxygen, which does not require special separation.

Other useful reagents include manganates and vanadates e.g. alkali metal or alkaline earth metal salts such as barium manganate or sodium vanadate. Chlorate oxidising agents can be used in the presence of manganese dioxide, the effective oxidising agent being, in fact, a permanganate. Osmium tetroxide can also be used as well as lead tetraacylates such as lead tetraacetate.

The allylic oxidation may be effected using molecular oxygen. Alternatively, compounds in which $R^2$ is a group

can be oxidised by a reagent of the type described for the oxidation of the conjugated isomer under isomerising conditions to effect preliminary isomerisation.

A base used to effect isomerisation of compounds wherein

compounds wherein $R^2$ is

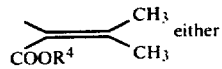

as a separate reaction or during oxidation, may be an inorganic base, such as an alkali metal or alkaline earth metal hydroxide or an alkali metal carbonate or alumina, or an organic base such as a tertiary amine, e.g. a trialkylamine such as N-ethylpiperidine or triethylamine, a heterocyclic base such as pyridine or collidine, or an alkali metal alkoxide. Inorganic bases will be reacted in aqueous or aqueous alcoholic media while nitrogen bases will in general be used in organic solvents such as hydrocarbons or chlorinated hydrocarbons, e.g. methylene chloride. Alkoxides will be used mainly in alcoholic solvents.

Oxidation of the decarboxylated product of formula III in which $R^2$ is the group

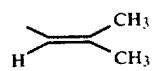

may be effected using any of the reagents described for the oxidation of the conjugated isomer of formula III in which $R^2$ is

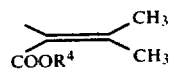

The oxidation is preferably effected in a solvent for the starting material. In general, a polar organic solvent is preferred, for example, a cyclic ether such as dioxan or tetrahydrofuran, a substituted amide solvent such as dimethylformamide or dimethylacetamide or, most preferably, an alkanol e.g. an alkanol containing 1–6 carbon atoms such as methanol, ethanol, or butanol. Water is often advantageously present. Where ozone is used, a hyroxylic solvent is required to decompose the ozonide initially formed although the oxidation can be effected in a non-hydroxylic solvent and hydrolysis effected during work-up. Inert solvents for the compound of formula III, for example hydrocarbons or chlorinated hydrocarbons, may also be present, together with a solvent facilitating oxidation such as a hydroxylic solvent.

The course of the reaction can be followed by thin layer chromatography and by the absence in the required product of the high-field signals in the n.m.r. due to the methyl groups in the side-chain $R^2$. Generation of the N-H group in the 1-position is denoted by appearance of a band in the infra red absorption of about 3440 cm$^{-1}$.

As stated above, $R^{1a}$ in compounds of formula I may be a blocked amino group including groups of formula —NHCOR, e.g. the 6-acylamino groups present in penicillins and protected amino groups, that is groups which can readily be converted into free amino groups, for example by hydrolysis, reduction or hydrogenolysis.

Where $R^{1a}$ is a protected amino group this may conveniently be one of the groups set out in the following table:

| Type | Example | Usual Name and Analogues etc. |
|---|---|---|
| Urethane | HNCOCH₂Ph ‖ O | Benzyloxycarbonyl, p-Methoxy |
| Urethane | HNCOC(CH₃)₃ ‖ O | t-Butoxycarbonyl |
| Urethane | HNCOCHPh₂ ‖ O | Diphenylmethoxy-carbonyl |
| Urethane | HNCO-(1-adamantyl) ‖ O | 1-Adamantyloxy-carbonyl |
| Arylmethyl-amino | HNCPh₃ | Trityl |
| Onium | NH₃⁺ | |
| Urethane | HN.CO.OCH₂CCl₃ | β,β,β-trichloroethoxy carbonyl |

Where $R^{1a}$ is a group —NHCOR or together with $R^{3a}$ is a group

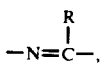

R may be defined generally as hydrogen or an organic group containing 1 to 20 carbon atoms. Thus the following main classes are especially suitable for the group RCO—:

(i) $R^uC_nH_{2n}$—CO where $R^u$ is aryl (carbocyclic or heterocyclic), cycloalkyl, substituted aryl, substituted cycloalkyl, cyclohexadienyl, or a non-aromatic or mesoionic heterocyclic group, and n is an integer from 1–4. Examples of this group include phenylacetyl; substituted phenylacetyl e.g. fluorophenylacetyl, nitrophenylacetyl, aminophenylacetyl, acetoxyphenylacetyl, methoxyphenylacetyl, methylphenylacetyl, or hydroxyphenylacetyl; N,N-bis(2-chloroethyl)aminophenyl-propionyl; thienyl-2- and -3-acetyl; 4-isoxazolyl and substituted 4-isoxazolylacetyl; pyridylacetyl; tetrazolylacetyl or a sydnoncacetyl group. The substituted 4-isoxazolyl group may be a 3-aryl-5-methyl isoxazol-4-yl group, the aryl group being e.g. phenyl or halophenyl e.g. chloro- or bromo- phenyl. An acyl group of this type is 3-o-chlorophenyl-5-methyl isoxazol-4-yl-acetyl.

(ii) $C_mH_{2m+1}$CO— where m is an integer from 1–7. The alkyl group may be straight or branched and, if desired, may be interrupted by an oxygen or sulphur atom or substituted by e.g. one or more halogen atoms, a cyano group, a carboxy group, an alkoxycarbonyl group, a hydroxy group or a carboxycarbonyl group (—CO.COOH). Examples of such groups include cyanacetyl, hexanoyl, heptanoyl, octanoyl, butylthioacetyl, chloroacetyl and trichloroacetyl groups.

(iii) $C_pH_{2p-1}$CO— where p is an integer from 2–7. The alkenyl group may be straight or branched and, if desired, may be interrupted by an oxygen or a sulphur atom. An example of such a group is allylthioacetyl.

(iv)

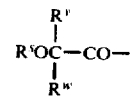

where $R^s$ is as defined above for $R^u$ or may be benzyl, and $R^v$ and $R^w$ which may be the same or different each represent hydrogen, phenyl, benzyl, phenethyl or lower alkyl. Examples of such groups include phenoxyacetyl, 2-phenoxy-2-phenylacetyl, 2-phenoxy propionyl, 2-phenoxybutyryl, 2-methyl-2-phenoxypropionyl, p-cresoxyacetyl and p-methylthiophenoxyacetyl.

(v)

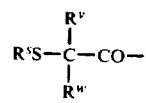

where $R^s$ $R^v$ and $R^w$ have the meanings defined under (iv). Examples of such groups include S-phenylthioacetyl, S-chlorophenylthioacetyl, S-fluorophenylthioacetyl, pyridylthioacetyl, and S-benzylthioacetyl.

(vi) $R^sZ(CH_2)_qCO$— where $R^s$ is as defined above, Z is an oxygen or sulphur atom and q is an integer from 2–5. An example of such a group is S-benzylthiopropionyl.

(vii) $R^uCO$— where $R^u$ has the meaning defined under (i). Examples of such groups include benzoyl, substituted benzoyl (e.g. aminobenzoyl), 4-isoxazolyl- and substituted 4-isoxazolylcarbonyl, cyclopentanecarbonyl, sydnonecarbonyl, naphthoyl and substituted naphthoyl (e.g. 2-ethoxynaphthoyl), quinoxalinylcarbonyl and substituted quinoxalinylcarbonyl (e.g. 3-carboxy-2-quinoxalinylcarbonyl). Other possible substituents for benzoyl include alkyl, alkoxy, phenyl, phenyl substituted by carboxy, alkylamido, cycloalkylamido, allylamido, phenyl(lower) alkyl amido, morpholinocarbonyl, pyrrolidinocarbonyl, piperidinocarbonyl, tetrahydropyridino, furfurylamido or N-alkyl-N-anilino, or derivatives thereof and such substituents may be in the 2- or 2- and 6-positions. Examples of such substituted benzoyl groups are 2,6-dimethoxybenzoyl, 2-methylamidobenzoyl and 2-carboxybenzoyl. Where the group $R^u$ represents a substituted 4-isoxazolyl group, the substituents may be as set out above under (i). Examples of such 4-isoxazolyl groups are 3-phenyl-5-methyl-isoxazol 4-yl carbonyl, 3-o-chlorophenyl-5-methyl isoxazol-4-yl carbonyl and 3-(2,6-dichlorophenyl)-5-methyl-isoxazol-4-yl carbonyl.

(viii)

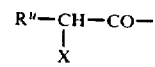

where $R^u$ has the meaning defined under (i) and X is amino, substituted amino (e.g. acylamido or a group obtained by reacting the α-aminoacylamido group of the 6-side chain with an aldehyde or ketone e.g. acetone, methylethylketone or ethyl acetoacetate), hydroxy, carboxy, esterified carboxy, triazolyl, tetrazolyl, cyano, halogeno, acyloxy (e.g. formyloxy or lower alkanoyloxy) or etherified hydroxy group. Examples of such acyl groups are α-aminophenylacetyl and α-carboxyphenylacetyl.

(ix)

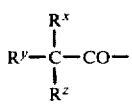

where $R^x$, $R^y$ and $R^z$ which may be the same or different may each represent lower alkyl, phenyl or substituted phenyl. $R^x$ can also be hydrogen. An example of such an acyl group is triphenylmethylcarbonyl.

(x)

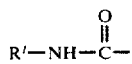

where $R^t$ is as defined above for $R^u$ or may be hydrogen, lower alkyl or halogen substituted lower alkyl, An example of such a group is $Cl(CH_2)_2NHCO$ (xi)

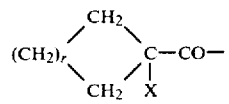

where X has the meaning defined under (viii) above and r is an integer of from 1 to 4. An example of such an acyl group is 1-aminocyclohexanecarbonyl.

(xii) $R^aCH(NH_2)(CH_2)_kCO$ where $R^a$ is as defined above for $R^u$ or is a hydrogen atom or an alkyl, aralkyl or carboxy group and k is an integer from 1 to 10 or $NH_2C_hH_{2h}Ar(CH_2)_gCO$ where g is zero or is an integer from 1 to 10, h is 0, 1 or 2 and Ar is an arylene group, e.g. p-phenylene or 1,4-naphthylene. Examples of such groups are disclosed in British Pat. No. 1,054,806. A group of this type is the p-aminophenylacetyl group. Other acyl groups of this type include those, e.g. δ-aminoadipoyl, derived from naturally occurring amino acids and derivatives thereof e.g. N-benzoyl-δ-aminoadipoyl or N-chloroacetyl-δ-aminoadipoyl.

(xiii) Substituted glyoxylyl groups of the formula $R^b.CO.CO—$ where $R^b$ is an aliphatic, araliphatic or aromatic group, e.g. a thienyl group, a phenyl group, or a mono-, di- or tri-substituted phenyl group, the substituents being, for example, one or more halogen atoms (F, Cl, Br, or I), methoxy groups, methyl groups or amino groups, or a fused benzene ring. Included in this group are also the α-carbonyl derivatives of the above substituted glyoxylyl groups, formed for example with hydroxylamine, semicarbazide, thiosemicarbazide, isoniazide or hydrazine.

Preferred amine protecting groups are the hydrocarbyloxycarbonyl groups (wherein the amino group forms part of a urethane), in particular alkoxycarbonyl groups such as methoxycarbonyl, ethoxycarbonyl and, most preferaby, t-butoxycarbonyl groups, which may carry substituents such as halogen atoms as in the 2,2,2-trichloroethoxycarbonyl group, as well as aralkoxycarbonyl groups such as benzyloxycarbonyl, p-methoxybenzyloxycarbonyl and diphenylmethoxycarbonyl groups. Cycloalkoxycarbonyl groups are also advantageous, especially the adamantyloxycarbonyl group. The p-nitrobenzyloxycarbonyl group, which can be selectively removed by reduction e.g. hydrogenolysis, is also useful. Such penicillins carrying protecting groups of this type may be prepared from 6-aminopenams by conventional methods for example by reaction with an appropriate haloformic ester.

Where $R^3$ in formula I is a group $—SR^5$, $R^5$ may, for example, be an alkyl group preferably containing 1–6 carbon atoms, e.g. a methyl, ethyl, butyl or iso-butyl group; an aralkyl group, preferably containing 1–6 carbon atoms in the alkyl portion, e.g. a benzyl, phenethyl or phenylpropyl group; a cycloalkyl group which may contain 5–7 carbon atoms in the ring and in which other aliphatic ring substituents containing up to 6 carbon atoms may be present; or a monocyclic aryl group such as a phenyl or substituted phenyl group. Such groups may be saturated or unsaturated and may carry substituents. The group $R^5$ may subsequently be made to cyclise with the β-lactam nitrogen or a grouping attached thereto as described in the copending Application Ser. No. 167,875 and so may advantageously possess substituents or reactive bonds permitting cyclisation with the β-lactam nitrogen or a group attached thereto. Such substituents include reactive ester substituents for example, halogen atoms and aromatic and aliphatic sulphonyl groups, carboxyl or esterified carboxyl groups or amino groups.

Where $R^3$ is an aliphatic, araliphatic or aromatic group, this may advantageously be one of the groups specifically described above in relation to $R^5$. A further useful group is the 3,4-dihydro-2H-pyran-5-yl grouping.

Where $R^3$ is an acyl group, this is preferably a group of the formula $R^6CO—$ where $R^6$ is an aliphatic, araliphatic or aromatic group which may advantageously be one of the groups specifically described for $R^5$.

Where $R^2$ in formula III is a group

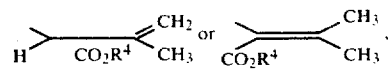

$R^4$ may be hydrogen or a blocking group to prevent the carboxyl group from entering into side reactions and can vary very widely since it does not appear in the final product.

In general $R^4$ may be hydrogen or an organic group having 1–20 carbon atoms. While the blocking group may be one which is readily removed by hydrolysis, this is not essential since it is not necessary that $R^4$ is removed during the removal of the side chain $R^2$ from the compound of formula III. It is preferred that $R^4$ is the residue of an alcohol or phenol, for example a cyclic or acyclic, straight or branched alkanol, advantageously containing 1–8 carbon atoms, e.g. methanol, ethanol, n-butanol, t-butanol, hexanol, octanol, cyclohexanol or adamantyl alcohol, which may carry substituents such as sulpho, esterified carboxyl, acyloxy, alkoxy, aralkoxy, alkylthio, alkoxyphenyl or aromatic heterocyclic groups or halogen atoms. Preferred substituted alkanols include 2,2,2-trichloroethanol and 4-pyridylmethanol. Residues of aralkyl alcohols are also useful, especially benzyl and substituted benzyl alcohols, e.g. those carrying electron-attracting groups such as sulpho or esterified carboxy groups which are readily split off by alkaline hydrolysis, and those carrying electron-donating groups such as alkoxy groups which are often readily removable by acid hydrolysis. Suitably substituted benzyl groups include p-methoxybenzyl, di-p-methoxyphenylmethyl, triphenylmethyl, diphenylmethyl and p-nitrobenzyl; closely analogous groups include benzoylmethyl, benzoyloxymethyl and furfuryl groups.

Residues of phenols include, for example, phenyl, p-methoxyphenyl and p-nitrophenyl groups.

Compounds of formula III in which $R^{1a}$ and $R^{3a}$ together represent a group

may be prepared from penicillanic acid 1-oxides by treatment with a trivalent phosphorus compound. The trivalent phosphorus compound may be a tri(lower alkyl)phosphite, e.g. trimethylphosphite.

The starting compounds of formula III in which $R^{1a}$ is a phenylacetamido group and $R^{3a}$ is an acyl group are also new compounds and thus constitute a further feature of the invention. They may be obtained from penicillanic acid 1-oxides by treatment with a trivalent phosphorus compound in the presence of an acylating agent, for example an anhydride or mixed anhydride of a carboxylic acid. The trivalent phosphorus compound may, for example, be a tri-lower alkyl phosphite, e.g. trimethyl phosphite. The reaction is preferably effected in an inert solvent, e.g. a hydrocarbon solvent such as benzene or toluene; or an ester such as ethyl acetate or an excess of acylating agent, where liquid, may serve as solvent. Improved yields may be obtained by including an alkaline earth metal carbonate in the medium, for example calcium carbonate.

Where $R^3$ is a group —$SR^5$, the starting material may be prepared by the methods described in the copending Application Ser. No. 167,848, filed July 30, 1971 now U.S. Pat. No. 3,872,086.

Where $R^3$ is an aliphatic, araliphatic or aromatic group, the starting material may be prepared by the process described in the copending Application Ser. No. 167,875, filed July 30, 1971, now abandoned.

Where $R^3$ is a dihydropyranyl group the starting material may be made by the method of Barton et al (Chem.Comms. 1970, pp 1683-4).

For a better understanding of the invention, the following Examples are given by way of illustration only. All temperatures are in °C. Column chromatography was carried out using Merck silica gel; the solvents used are given in the individual Examples. NMR spectra were obtained on a Varian HA 100 instrument, unless otherwise stated. The integrals agreed with the numbers of protons indicated. Signs were not determined for the coupling constants (J).

EXAMPLE 1

(a) 2',2',2'-Trichloroethyl α-Isopropenyl-α-[3-Benzyl-4,7-diaza-6-oxo-2-thia-1(R),5(R)-bicyclo[3,2,0]-hept-3-en-7-yl]-acetate.

2,2-Dimethyl-3α-(2,2,2-trichloroethoxycarbonyl)-6β-phenylacetamidopenam, 1β-oxide (13.6 g., 0.0304 mole) was refluxed with trimethyl phosphite (10 ml., 0.085 L mole) in benzene (500 ml.) for 39 hours. After washing with water (4×100 ml.) the mixture was evaporated to give a pale-yellow solid which was recrystallised from methanol yielding 2',2',2'-trichloroethyl α-isopropenyl-α-[3-benzyl-4,7-diaza-6-oxo-3-thia-1(R),5(R)-bicyclo[3,2,0]-hept-3-en-7-yl]-acetate (5.65 g., 45%), m.p. 150°, $[\alpha]_D^{27} - 121°$ (c 1.00, dioxan), $\nu_{max}$.(CHBr$_3$) 1768 (β-lactam), 1755 (CO$_2$CH$_2$CCl$_3$), 915 (=CH$_2$), and 766 cm.$^{-1}$ (CCl$_3$), τ (CDCl$_3$) 2.71 (5-proton singlet; phenyl protons), 4.01 and 4.12 (two 1-proton doublets, J 4 Hz.; β-lactam protons), 4.89 and 4.98 (two 1-proton doublets, J 1 Hz.; =CH$_2$), 5.02 (1-proton singlet;

5.20 (2-proton singlet; —CH$_2$CCl$_3$), 6.12 (2-proton singlet; —CH$_2$Ph), and 8.27 (3-proton singlet; —CH$_3$) [Found: C, 48.1; H, 3.9; N, 6.4; S, 7.1; Cl, 23.2. C$_{18}$H$_{17}$N$_2$SO$_3$Cl$_3$ (447.5) requires C, 48.3; H, 3.8; N, 6.3; S, 7.2; Cl, 23.75%].

The methanolic mother-liquors from the recrystallisation contained starting material (13%) and 2',2',2'-trichloroethyl α-isopropylidenyl-α-[3-benzyl-4,7-diaza-6-oxo-2-thia-1(R),5(R)-bicyclo[3,2,0]-hept-3-en-7-yl]-acetate (42%). (tlc and nmr spectrum in agreement with a mixture of these two compounds; see Stage (b)).

(b) 2',2',2'-Trichloroethyl α-isopropylidenyl-α-[3-benzyl-4,7-diaza-6-oxo-2-thia-1(R),5(R)-bicyclo[3,2,0]-hept-3-en-7-yl]-acetate.

2',2',2'-Trichloroethyl α-isopropenyl-α-[3-benzyl-4,7-diaza-6-oxo-2-thia-1(R),5(R)-bicyclo[3,2,0]-hept-3-en-7-yl]-acetate (2 g., 0.0045 mole) was stirred with triethylamine (0.2 ml., 00015 mole) in ethyl acetate (30 ml.) at 21° for 30 minutes. The mixture was filtered through silica gel (100 g.), eluting with ethyl acetate (150 ml.). This solution was evaporated to give 2',2',2'-trichloroethyl α-isopropylidenyl-α-[3-benzyl-4,7-diaza-6-oxo-2-thia-1(R),5(R)-bicyclo[3,2,0]-hept-3-en-7-yl]-acetate (2.07 g., 103%) as a colourless oil, $[\alpha]_D^{27} + 29°$ (c 1.00, dioxan), $\nu_{max}$.(CHBr$_3$), 1760 (β-lactam), 1730 (COOCH$_2$CCl$_3$), 1610

and 760 cm.$^{-1}$ (—CCl$_3$), τ (CDCl$_3$) 2.65 (5-proton singlet; phenyl protons), 3.86 (2-proton singlet; β-lactam protons), 5.01 and 5.39 (two 1-proton doublets, branches of a quartet, J 12 Hz.; —CH$_2$—CCl$_3$), 6.09 (2-proton singlet; —CH$_2$Ph), and 7.71 and 8.31 [two 3-proton singlets; =C(CH$_3$)$_2$].

(c) 3-Benzyl-4,7-diaza-6-oxo-2-thia-1(R),5(R)-bicyclo[3,2,0]-hept-3-ene (i) By Ozonolysis.

Ozonised oxygen (35 liters per hour) was passed through a solution of 2',2',2'-trichloroethyl α-isopropylidenyl-α-[3-benzyl-4,7-diaza-6-oxo-2-thia-1(R),5(R)-bicyclo[3,2,0]-hept-3-en-7-yl]-acetate (5g., 0.011 mole) in methanol (100 ml.) with vigorous stirring a 0° for 40 minutes; tlc then indicated no starting material remaining. After exhausting the solution of ozone, sodium metabisulphite (10 g.) in water (50 ml.) was added. The methanol was evaporated at reduced pressure and the aqueous residue adjusted to pH 8 with sodium carbonate. This mixture was extracted with ethyl acetate (3×100 ml.), washed with water (2×100 ml.), and evaporated to an off-white solid (2.13 g.). This was slurried with ether (50 ml.) to give 3-benzyl-4,7-diaza-6-oxo-2-thia-1(R),5(R)-bicyclo[3,2,0]-hept-3-ene (1.11 g., 56%) as a white solid, m.p. 181° to 183°, $[\alpha]_D^{27} + 84.5°$ (c 1.00, tetrahydrofuran), tlc R$_F$ 0.53 (ethyl acetate:benzene=2:1); $\nu_{max}$. (Nujol) 3190 (NH), 1735 and 1710 cm.$^{-1}$ ($\beta$-lactam), NMR (100 MHz, d$_6$—DMSO, $\tau$) 1.10 (NH), 2.73 (C$_6$H$_5$), 4.06 (1-proton multiplet, H$_5$), 4.45 (doublet, J=4 Hz, H$_1$), 6.10 (PhC$\underline{H}_2$).

(ii) By Oxidation with Potassium Permanganate.

Potassium permanganate (1.5 g., 0.0096 mole) and magnesium sulphate (1.1 g.) in water (30 ml.) were added to a vigorously stirred solution of 2',2',2'-trichloroethyl $\alpha$-isopropylidenyl-$\alpha$-[3-benzyl-4,7-diaza-6-oxo-2-thia-1(R),5(R)-bicyclo[3,2,0]-hept-3-en-7-yl]-acetate (5.16 g., 0.0115 mole) in ethanol (60 ml.) at 20°. Further potassium permanganate (4×1 g. portions, 0.025 mole) was added at ½-hourly intervals until tlc. indicated no starting material remaining. The ethanol was evaporated at reduced pressure and the aqueous residue adjusted to pH 8 with sodium carbonate. After stirring with ethyl acetate (100 ml.) for 10 minutes, the mixture was filtered, the residue being washed thoroughly with ethyl acetate (100 ml). The organic layer was separated and the aqueous layer extracted with ethyl acetate (2×100 ml.). The combined organic layers were washed with water (3×100 ml.) and evaporated to give a brown solid (2.03 g.). This was chromatographed on silica gel (200 g.) in ethyl acetate: petrol (b.p. 60° to 80°) to give 3-benzyl-4,7-diaza-6-oxo-2-thia-1(R),5(R)-bicyclo[3,2,0]-hept-3-ene (1.61 g., 63.7%), m.p. 181° to 183°, $[\alpha]_D^{27}$+65° (c 1.00, tetrahydrofuran), tlc. R$_F$ 0.52 (ethyl acetate:benzene=2:1). Nmr spectrum in agreement with standard.

EXAMPLE 2

2',2',2'-Trichloroethyl (3R,4R)-$\alpha$-isopropenyl-$\alpha$-[4-acetylthio-3-phenylacetamidoazetidin-2-on-1-yl]acetate 2',2',2'-Trichloroethyl (1S,3R,5R,6R)-2,2-dimethyl-6-phenylacetamidopenam-3-carboxylate (19.26 g., 0.04 mole) was refluxed with acetic anhydride (19.1 ml., 0.2 mole) and trimethylphosphite (9.44 ml., 0.08 mole) in toluene (200 ml.) for 5 hours. After washing with water (3×200 ml.), the mixture was evaporated to a yellow gum which was slurried with ether to separate 2',2',2'-trichloroethyl (1R,5R)-$\alpha$-isopropenyl-$\alpha$-[3-benzyl-4,7-diaza-6-oxo-2-thia-bicyclo[3,2,0]hept-3-en-7-yl]-acetate (1.56 g.). The ether filtrate was evaporated and chromatographed on silica gel eluting with 30% ethyl acetate in benzene. After further bicycloheptene (7.83 g.), the solvent eluted 2',2',2'-trichloroethyl (3R,4R)-$\alpha$-isopropenyl-$\alpha$-[4-acetylthio-3-phenylacetamidoazetidin-2-on-1-yl]acetate as a foam (10.7 g., 52%), $[\alpha]_D^{20}$−37.5° (C 1.00, dioxan), $\nu_{max}$(CHBr$_3$) 3448 (NH), 1770 ($\beta$-lactam), 1760 (ester), 1700 (COCH$_3$), 1682 and 1513 (amide), and 913 cm$^{-1}$ (=CH$_2$), NMR (CDCl$_3$, $\tau$) 2.68 (singlet; phenyl protons), 3.60 (doublet, J 7 Hz; CONH), 4.90 (doublet, J 5 Hz; C-4H), 4.62 (double doublet, J 7,5 Hz; C-3H), 4.88, 4.94 and 5.19 (signals due to

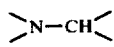

and =CH$_2$), 5.12 and 5.28 (doublets, branches of a quartet, J 12 Hz; —CH$_2$CCl$_3$), 6.40 (singlet; PhCH$_2$—), 7.78 (singlet; COCH$_3$), and 8.10 (singlet; —CH$_3$).

EXAMPLE 3 (Part 1)

2',2',2'-Trichloroethyl(3R,4R)-$\alpha$-isopropylidene-$\alpha$-(4-acetylthio-3-phenylacetamidoazetidin-2-on-1-yl) acetate 2',2',2'-Trichloroethyl(3R,4R)-$\alpha$-isopropenyl-$\alpha$-(4-acetylthio-3-phenylacetamidoazetidin-2-on-1-yl)acetate (1.28 g., 0.025 mole) was stirred with triethylamine (0.13 ml.) in ethyl acetate (10 ml.) at 20° for 30 minutes. The mixture was filtered through silica gel, eluting with ethyl acetate. Evaporation of the ethyl acetate gave 2',2',2'-trichloroethyl(3R,4R)-$\alpha$-isopropylidene $\alpha$-(4-acetylthio-3-phenylacetamidoazetidin-2-on-1-yl)acetate as a foam (1.14 g.) 89%), $[\alpha]_D^{20}$+11.6° (c 1.00 dioxan), $\nu_{max}$.(CHBr$_3$) 3435 (NH), 1773 ($\beta$-lactam), 1732 (ester), ~1689 (COCH$_3$), and 1689 and 1512 cm$^{-1}$ (amide), NMR (CDCl$_3$ $\tau$) 2.67 (singlet; phenyl protons), 3.85 (doublet, J 7 Hz; CONH), 3.94 (doublet J 7 Hz; C-4H), 4.85 (double doublet J 7,5 Hz; C-3H), 5.11, 5.28 (doublets, branches of a quartet, J 12 Hz; CH$_2$CCl$_3$), 6.35 (singlet; PhC$\underline{H}_2$—), 7.71 and 7.88 [singlets; =C(CH$_3$)$_2$], and 7.83 (singlet; COCH$_3$).

EXAMPLE 3 (Part 2)

(3R,4R)-4-Acetylthio-3-phenylacetamidoazetidin-2-one

2',2',2'-Trichloroethyl(3R,4R)-$\alpha$-isopropylidene-$\alpha$-(4-acetylthio-3-phenylacetamidoazetidin-2-on-1-yl)acetate (1.1 g., 0.0022 mole) was stirred in methanol (20 ml.) at 0° while a stream of ozonised oxygen (35 litres/hr.) was passed through for 20 minutes. Sodium metabisulphite (0.5 g.) in water (10 ml.) was added and the methanol evaporated under reduced pressure. The aqueous residue was extracted with ethyl acetate (3×100 ml.) and the combined organic layers were washed with water (3×100 ml.). The ethyl acetate was evaporated and the residual yellow oil was diluted with ether (5 ml.). This solution deposited crystals of (3R,4R)-4-acetylthio-3-phenylacetamidoazetidin-2-one (0.15 g., 25%), $[\alpha]_D^{20}$+57.5° (c 1.00 dioxan), m.p. 110° to 111°, $\nu_{max}$. (CHBr$_3$) 3690 (water), 3420 and 3330 (NH), 1780 ($\beta$-lactam), 1700 (COCH$_3$), and 1680 and 1510 cm$^{-1}$ (CONH), NMR (d$_6$—DMSO, $\tau$) 1.04 (doublet, J 8 Hz; C-3 N$\underline{H}$), 1.13 (singlet; $\beta$-lactam N$\underline{H}$), 2.67 (singlet; phenyl protons), 4.49 (doublet, J 4 Hz; C-4H), 4.66 (double doublet, J 8,4 Hz) C-3H), 6.48 (singlet; PhCH$_2$—) and 7.68 (singlet; COCH$_3$) [Found: C, 54.5; H, 5.0; N, 9.7; S, 10.1. C$_{13}$H$_{14}$N$_2$O$_3$S.O.5H$_2$O (287) requires C, 54.3; H, 5.2; N, 9.8; S, 11.1%].

EXAMPLE 4

(1R,5R)-4,7-Diaza-6-oxo-3-phenoxymethyl-2-thiabicyclo[3,2,0]-hept-3-ene

A solution of 2",2",2"-trichloroethyl-2-isopropylidene-2-[(1'R,5'R)-4',7'-diaza-6'-oxo-3'-phenoxymethyl-2'-thiabicyclo[3',2',0']-hept-3'-ene-7'-yl]-acetate (10 g., 0.022 mole) (Cooper and Jose, J. Amer. Chem. Soc., 1970, 92, 2575) in methanol (400 ml.) was cooled to 0° and ozone passed for 1 hour through the stirred solution, after which thin-layer chromatography indicated the absence of starting material. A solution of sodium metabisulphite (6.5 g) in water (20 ml) was then added and the mixture evaporated to a small volume under reduced pressure. Treatment with saturated sodium hydrogen carbonate solution, addition of ethyl acetate, separation of the organic phase, washing with water, drying, and evaporation gave the title compound as colourless crystals (1.3 g., 25.5%) mp 152° to 153°. $[\alpha]_D^{22}+107°$ (c 1, tetrahydrofuran $\nu_{max}$ (CHBr$_3$) 3386 (NH), 1780 ($\beta$-lactam), 1619 (C=N), and 750 cm$^{-1}$ (Ph) NMR (60 MHz, CDCl$_3$ $\tau$) 1.68 (NH), 2.5 to 3.2 (Ph), 3.95 (multiplet 5-H), 4.49 (doublet, J=5 Hz, 1-H), and 5.05 (O C$\underline{H}_2$ Ph). (Found: C, 56.6; H, 4.5; N, 11.7; S, 13.2. C$_{11}$H$_{10}$N$_2$O$_2$S requires C, 56.4; H, 4.3; N, 12.0; S, 13.7%).

We claim:

1. A process for the preparation of a compound of the formula

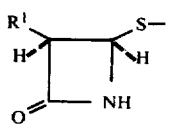

I wherein R$^{1a}$ and R$^{3a}$ represent groups R$^1$ and R$^4$ respectively where R$^1$ is a blocked amino group of formula —NHCOR where —COR is an acyl group having 1 to 20 carbon atoms and R$^3$ is an acyl group of formula R$^6$CO— where R$^6$ is an alkyl group of 1 to 6 carbon atoms, a phenylalkyl group wherein the alkyl portion has 1 to 6 carbon atoms, a cycloalkyl group of 5 to 7 carbon atoms or a phenyl group; an alkyl group of 1 to 6 carbon atoms, a phenyl group; a phenylalkyl group wherein the alkyl portion has 1 to 6 carbon atoms; a group —SR$^5$ where R$^5$ is an alkyl group of 1 to 6 carbon atoms, a phenylalkyl group wherein the alkyl portion has 1 to 6 carbon atoms, a cycloalkyl group of 5 to 7 carbon atoms or a phenyl group; or a group of formula

II where R$^1$ is as defined above or R$^{1a}$ and R$^{3a}$ together represent the group

where R is the residue of an acyl group —COR which acyl group has from 1 to 21 carbon atoms, the carbon atom of the group

—N=C—
  |
  R being bonded to the sulphur atom of the compound of formula I, which process consists of reacting a compound of formula

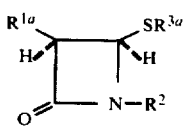

III wherein R$^2$ is a group

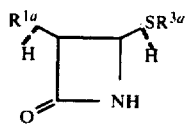

where R$^4$ is hydrogen or a carboxyl blocking group and R$^{1a}$ and R$^{3a}$ are as defined above except that R$^3$ can be a group of formula

IV but not a group of formula II with an alkali metal or alkaline earth metal permanganate.

2. A process as claimed in claim 1 wherein the permanganate is potassium permanganate.

3. A process as claimed in claim 1 wherein R$^2$ is a group of formula

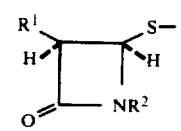

wherein R$^4$ is as defined in claim 1 and the reaction is effected under basic conditions to first isomerise the group R$^2$ to a group of formula

where R$^4$ is as defined in claim 1.

4. A process as claimed in claim 3 wherein the basic conditions are provided by an alkali metal or alkaline earth metal hydroxide, an alkali metal carbonate, alumina, a trialkyl amine, pyridine, collidine or an alkali metal alkoxide.

5. A process as claimed in claim 1 wherein the compound of formula III is a compound in which R$^2$ represents a group wherein R$^4$ is hydrogen or is a 2,2,2-trichloroethyl, 4-pyridylmethyl, p-methoxybenzyl, di-p-methoxyphenylmethyl, triphenylmethyl, diphenylmethyl, p-nitrobenzyl, benzoylmethyl, benzoyloxymethyl, furfuryl, phenyl, p-methoxyphenyl, or p-nitrophenyl group.

6. A process as claimed in claim 1 wherein a compound of formula III in which R$^{1a}$ and R$^{3a}$ together represent the group

where R is the residue of an acyl group —COR which acyl group has 1 to 21 carbon atoms is reacted with said permanganate whereby a compound of formula I in which R$^{1a}$ and R$^{3a}$ are as defined for the compound of formula III is obtained.

7. A process as claimed in claim 6 wherein R represents a benzyl or phenoxymethyl group.

8. A process as claimed in claim 1 wherein the compounds of formulae I and III are compounds wherein $R^{1a}$ is a urethane, phenylonethylamino, or onium group.

9. A process as claimed in claim 1 in which $R^{1a}$ is a phenylacetamido group or a phenoxyacetamido group.

10. The process of claim 1, wherein the R of the acyl group —COR is H, or a group $R^u(O)_rC_nH_{2n}$, wherein $R^u$ is $C_{5-7}$ cycloalkyl, cyclohexadienyl, phenyl, fluorophenyl, nitrophenyl, aminophenyl, acetoxyphenyl, methoxyphenyl, methylphenyl, hydroxyphenyl or N,N-bis(2-chloro-ethyl) aminophenyl; r is 0 or 1 and n is an integer from 1 to 4.

* * * * *